(12) United States Patent
Taylor

(10) Patent No.: US 9,393,121 B2
(45) Date of Patent: Jul. 19, 2016

(54) PROSTHESIS

(71) Applicant: FINSBURY (DEVELOPMENT) LIMITED, Leatherhead, Surrey (GB)

(72) Inventor: Andrew Clive Taylor, Chichester (GB)

(73) Assignee: FINSBURY (DEVELOPMENT) LIMITED (GB)

( * ) Notice: Subject to any disclaimer, the term of this patent is extended or adjusted under 35 U.S.C. 154(b) by 0 days.

(21) Appl. No.: 14/516,895

(22) Filed: Oct. 17, 2014

(65) Prior Publication Data

US 2015/0034597 A1 Feb. 5, 2015

Related U.S. Application Data

(62) Division of application No. 13/576,582, filed as application No. PCT/GB2011/050188 on Feb. 3, 2011, now Pat. No. 8,888,860.

(30) Foreign Application Priority Data

Feb. 4, 2010 (GB) .................................. 1001830.7

(51) Int. Cl.
  *A61F 2/34* (2006.01)
  *A61L 27/18* (2006.01)
  (Continued)

(52) U.S. Cl.
  CPC ... *A61F 2/34* (2013.01); *A61F 2/28* (2013.01); *A61F 2/30942* (2013.01); *A61L 27/18* (2013.01);
  (Continued)

(58) Field of Classification Search
  CPC .............. A61F 2/28; A61F 2/32; A61F 2/34; A61F 2/30767; A61F 2/3094; A61F 2/30942; A61F 2/30965; A61F 2002/30006; A61F 2002/30011; A61F 2002/30013; A61F 2002/30028; A61F 2002/30062; A61F 2002/30324; A61F 2002/30594; A61F 2002/30733; A61F 2002/3092; A61F 2002/30925; A61F 2002/3097; A61F 2002/30971; A61F 2002/3487; A61F 2310/00796; A61L 27/18; A61L 27/32; A61L 27/50; A61L 27/54; A61L 27/56; A61L 2300/112; A61L 2300/608; B29C 45/16
  See application file for complete search history.

(56) References Cited

U.S. PATENT DOCUMENTS 5,549,700 A 8/1996 Graham
8,888,860 B2 * 11/2014 Taylor .................... A61L 27/18
                                                                  623/22.21

(Continued)

FOREIGN PATENT DOCUMENTS

EP 1205160 A2 5/2002
EP 1647242 A1 4/2006
(Continued)

OTHER PUBLICATIONS

Kinburn, A., "Taking a PEEK at Material Options for Orthopedics"; Medical Design Technology Magazine, Jan. 2009, p. 26; vol. 13, Issue 1, Rockaway NJ 07866.
(Continued)

*Primary Examiner* — Jiong-Ping Lu

(57) ABSTRACT

A prosthesis comprising: an inner layer formed from a polyaryletherketone; a first outer layer adjacent to said inner layer formed from a porous polyaryletherketone, at least some of said pores having located therein material to promote osteointegration; and a second outer layer adjacent to said first outer layer formed from a porous polyaryletherketone, a portion of said pores being free of material to promote osteointegration. The invention also relates to a method of manufacture of the prosthesis. In an alternative arrangement, the prosthesis comprises: an inner layer formed from a polyaryletherketone; a first outer layer adjacent to said inner layer formed from a porous polyaryletherketone, at least some of said pores having located therein material to promote osteointegration having a crystallinity of from about 60% to about 90%; and a second outer layer adjacent to said first outer layer formed from a porous polyaryletherketone.

8 Claims, 3 Drawing Sheets

(51) Int. Cl.
- *A61L 27/54* (2006.01)
- *A61L 27/56* (2006.01)
- *A61F 2/28* (2006.01)
- B29C 45/16 (2006.01)
- *A61F 2/30* (2006.01)
- *B29K 71/00* (2006.01)
- *B29K 511/06* (2006.01)
- *B29L 9/00* (2006.01)
- *B29L 31/00* (2006.01)

(52) U.S. Cl.
CPC ............ *A61L 27/54* (2013.01); *A61L 27/56* (2013.01); *B29C 45/16* (2013.01); *A61F 2/30965* (2013.01); *A61F 2002/30028* (2013.01); *A61F 2002/30062* (2013.01); *A61F 2002/3092* (2013.01); *A61F 2002/3097* (2013.01); *A61F 2002/30324* (2013.01); *A61F 2002/30594* (2013.01); *A61F 2002/30733* (2013.01); *A61F 2002/30971* (2013.01); *A61F 2002/3487* (2013.01); *A61F 2310/00796* (2013.01); *A61L 2300/112* (2013.01); *A61L 2300/608* (2013.01); *B29K 2071/00* (2013.01); *B29K 2511/06* (2013.01); *B29K 2995/004* (2013.01); *B29L 2009/00* (2013.01); *B29L 2031/7532* (2013.01)

(56) References Cited

U.S. PATENT DOCUMENTS

| | | |
|---|---|---|
| 2007/0100447 A1 | 5/2007 | Steinberg |
| 2008/0161927 A1 | 7/2008 | Savage |
| 2009/0192610 A1 | 7/2009 | Case |
| 2009/0276053 A1 | 11/2009 | Brown |
| 2009/0280156 A1* | 11/2009 | Hotokebuchi ...... A61F 2/30767 424/423 |

FOREIGN PATENT DOCUMENTS

| | | | |
|---|---|---|---|
| GB | 2463066 A | 3/2010 | |
| WO | WO 2007035968 A2 | 3/2007 | |
| WO | WO 2007051307 A2 | 5/2007 | |
| WO | WO 2009097412 A2 | 8/2009 | |
| WO | WO 2009097968 A2 | 8/2009 | |
| WO | WO2010007424 * | 1/2010 | ............ C08J 3/20 |
| WO | WO 2010007424 A1 | 1/2010 | |

OTHER PUBLICATIONS

Manley, M.T., et al., "Biomechanics of a PEEK Horseshoe-Shaped Cup: Comparisons with a Predicate Deformable Cup"; 53rd Annual Meeting of the Orthopaedic Research Society, Feb. 11, 2007; Poster No. 1717; San Diego, CA.

* cited by examiner

PROSTHESIS

CROSS REFERENCE TO RELATED APPLICATION

This application is a divisional of U.S. patent application Ser. No. 13/576582, filed Feb. 3, 2011, (now U.S. Pat. No. 8,888,860, granted Nov. 18, 2014), which is herein incorporated by reference in its entirety.

The present invention relates to a prosthesis. More particularly, it relates to an acetabular prosthesis.

The efficient functioning of the hip joint is extremely important to the well-being and mobility of the human body. Each hip joint is comprised by the upper portion of the femur which terminates in an offset bony neck surmounted by a ball-headed portion which rotates within the acetabulum in the pelvis. Diseases such as rheumatoid- and osteo-arthritis can cause erosion of the cartilage lining of the acetabulum so that the ball of the femur and the hip bone rub together causing pain and further erosion. Bone erosion may cause the bones themselves to attempt to compensate for the erosion which may result in the bone becoming misshapen.

Operations to replace the hip joint with an artificial implant are well-known and widely practiced. Generally, the hip prosthesis will be formed of two components, namely: an acetabular component which lines the acetabulum; and a femoral component which replaces the femoral head. The femoral component may be total femoral head replacement in which case the component includes a head, neck and a stem which in use is inserted into the end of a prepared femur. Alternatively, where appropriate, the femoral head component may be a resurfacing prosthesis which is attached to the head of the femur once it has been suitably machined.

In an operation to insert a prosthetic acetabulum in a patient's pelvis the surgeon first uses a reamer to cut a cavity of appropriate size in the patient's pelvis. An acetabular cup is then inserted into the cavity. By "appropriate size" is meant a size which is selected by the surgeon as being the most appropriate for that particular patient. Normally, it is desirable to retain as much of the original healthy bone surface as possible.

Commercially available acetabular cups are sold in a range of sizes to suit the needs of individual patients. Generally, acetabular cups are available in sizes of from 42 mm to 62 mm diameter with 2 mm increments between neighboring sizes.

There are a number of different types of prosthetic acetabular cups. One type of cup is those made from polyethylene. They are generally cemented into the acetabulum and require only light pressure to seat them in the cement.

One alternative cup type has a polyethylene liner unit for articulation with the femur and a metal shell for insertion into the pelvic cavity. These cups with metal shells may be implanted without cement such that they rely on a jam fit between the metal shell and the patient's acetabulum. However, in some arrangements, screws may be used to secure the cup shell in position in the pelvis before the liner is applied into position. The insertion of the metal shell into the pelvis requires considerable force. As the surgeon applies this force, there is a risk that the metal shell can become damaged or deformed. There is also a possibility that during the application of the force, the shell may be moved so that it is not in the optimum alignment in the acetabulum. Often the metal shells have outer surfaces or coatings which encourage bone to grow into them over time.

With this type of prosthesis, the polyethylene liner unit is snapped or screwed into the metal shell after the metal shell has been seated in the acetabulum. Thus the inner surface of the liner forms the socket part of the joint.

More recently, ceramics have been used as an alternative to the plastics liner. In this arrangement, the metal shell, which is generally formed from titanium, is inserted into the acetabulum. The ceramic liner is then inserted into the shell.

Whilst these various prior art arrangements offer relief to patients from the pain of the worn joint, there is a continuing desire to provide prostheses which provide improved results to the patient, particularly in terms of wear. This is particularly important for younger patients where revision operations may be required if the prosthesis itself becomes worn or becomes loosened in the acetabulum. There is therefore an ongoing need for new materials and/or new structures for prostheses which more closely mimic the natural bone while minimizing the wear problems thereof.

Polyetheretherketone (PEEK) polymers have been suggested as being suitable materials for use in orthopaedic implants. This material is discussed in "Taking a PEEK at Material Options for Orthopedics", Kinburn A., Medical Design Technology Magazine; 1 Jan. 2009 page 26ff. It is suggested that particular advantages can be obtained if the PEEK is reinforced with carbon fibres. The use of PEEK in a horseshoe-shaped cup is discussed in "Biomechanics of a PEEK Horseshoe-Shaped Cup: Comparisons with a Predicate Deformable Cup" Manley, M. T., et al Poster No 1717 at $53^{rd}$ Annual Meeting of the Orthopaedic Research Society.

WO2009/097412 suggests that PEEK can be useful in a multi-layered hemispherical prosthesis. The multi-layered system comprises an outer layer formed from a porous metal and an inner layer formed from a polyaryletherketone in which the polyaryletherketone at least partially permeates the pores of the first material. The Applicants suggest that this arrangement allows the two layers to be securely bonded together. They also suggest that the prosthesis has a lower stiffness than that achieved for prior art arrangements.

An example of the use of PEEK in a prosthetic acetabular cup is described in EP 1647242. In one described embodiment, the prosthesis comprises an inner bearing surface made from a PEEK/carbon fibre composite. An outer coating is then formed on the inner bearing surface by sputtering PEEK using a plasma torch. This outer coating forms a barrier backing layer. The size of the PEEK particles at the start of the sputtering process is small and is increased during the process so that a porous structure is produced. This porous layer is coated with hydroxyapatite as a continuous layer. This coating is provided to create a barrier between the composite materials and the bone cells, provide an appropriate roughness for bone attachment and/or provide open porosity for bone cell ingrowth.

US2008/161927 describes a device for promoting fusion between first and second vertebra which comprises a first solid region formed from PEEK and a first porous region bonded to the first solid region. The first porous region has a porous PEEK architecture. A bone growth promoting material, such as hydroxyapatite, may be applied to the first porous region.

An implant formed from PEEK comprising a plurality of interconnected pores is described in WO2007/051307. Also described is a method of making the porous material in which a first material is mixed with a second material which has a melting point that is higher than the first material, heating the mixture under pressure to a temperature between a melting point of the first material and a melting point of the second material, cooling the molten mixture until it hardens and removing the second material from the first material. There is also described a method which comprises mixing a fluid material with a solid particulate sacrificial material to form a mixture, hardening the mixture and removing the solid particulate from the hardened mixture to leave a plurality of interconnected pores. Generally coarse table salt is used as the sacrificial material Whilst these proposals go some way to addressing the problems of the prior art there is still a need for alternative, preferably improved, arrangements.

According to the present invention there is provided a prosthesis comprising:
  an inner layer formed from a polyaryletherketone;
  a first outer layer adjacent to said inner layer formed from a porous polyaryletherketone, at least some of said pores having located therein material to promote osteointegration; and
  a second outer layer adjacent to said first outer layer formed from a porous polyaryletherketone, a portion of said pores being free of material to promote osteointegration.

The prosthesis of the present invention offers various advantages over prior art arrangements. The prosthesis is lightweight, while having the required strength. In addition, it has improved wear resistance over prior art arrangements.

Whilst a metal coating layer, such as a layer of titanium, may be located between the inner layer and the first outer layer this is not generally preferred. Where such a metal layer is present it will generally be thin, of the order of no more than about 1 mm.

Since metal is not used in the outer layer, the production costs are substantially reduced over prior art prosthesis. A further advantage of not using a metal outer surface is that the finished prosthesis will have some flexibility and will generally have a flexibility that is similar to that of natural bone. Where the prosthesis is for use in the acetabulum, it will have a similar flexibility to that of the pelvis. A still further advantage of not using a metal outer layer is that the finished prosthesis will have a softer edge such that the effect of any impingement is reduced.

The polyaryletherketone in the outer layers and the inner layer may be the same or different. In one preferred arrangement, the polyaryletherketone in each layer is polyetheretherketone.

The first and second outer layers may be discrete layers or may be regions with in a single layer such that they are contiguous.

In one arrangement, the polyaryletherketone may be reinforced. Generally only the inner layer will be reinforced although in some arrangements at least one of the outer layers may include reinforcement. Any suitable material may be used to reinforce the polyaryletherketone although carbon fibre will generally be used as the reinforcing material.

Whilst the pores in the porous outer layer may be discrete separated pores, at least some pores are preferably interconnected with other pores. Thus, in a particularly preferred arrangement, groups of pores are interconnected to form a labyrinth. This porous structure not only allows bone ingrowth from its outer surface, but also allows integration of the polyaryletherketone from the inner layer into the first outer layer and the first outer layer into the second out layer thereby ensuring the layers are locked together Any suitable material may be used as the material to promote bone ingrowth. Suitable materials include hydroxyapatite, calcium phosphate, tricalcium phosphate, and calcium carbonate, with hydroxyapatite being particularly preferred. Where a pore or pores have located therein material to promote osteointegration, the bone ingrowth material may completely fill the pore or may partially fill the pore. In one arrangement, some of the pores will be partially filled and others completely filled. In a further arrangement, rather than the pores being filled or partially filled, at least some of the pores may have at least one of their walls, or a part thereof, coated with the bone ingrowth material. In a still further arrangement, some pores may be filled, some may be partially filled, while others may have at least one of their walls, or a part thereof, coated with the bone ingrowth material.

At least some of the pores in the second outer layer are free of material to promote osteointegration. In one arrangement, more than about 50% of the pores in the second outer layer are free of material to promote osteointegration. In another arrangement, from about 60% to about 80% of the pores are free of material to promote osteointegration. In a still further arrangement, the pores in the outer layer are substantially free of material to promote osteointegration.

At least some of the pores will include material to promote osteointegration within them. In one arrangement at least about 20% of the pores will include material to promote osteointegration. In another arrangement at least about 50% or from about 60% to about 80% of the pores include material to promote osteointegration. In a still further arrangement substantially all of the pores in the first outer layer include material to promote osteointegration.

Without wishing to be bound by any theory it is believed that having the material to promote osteointegration located in the inner pores facilitates drawing the bone through the labyrinth of pores and into the first outer layer thereby firmly holding the prosthesis in position.

In one arrangement, the crystallinity of the material to promote osteointegration, generally hydroxyapatite, will be different between the first and second outer layers. In one arrangement, a material having a higher crystallinity will be present in the first outer layer and a material having a lower crystallinity will be present in those pores of the second outer layer which include material to promote osteointegration. The actual crystallinities selected may any that are suitable provided that relatively the more crystalline is located in the first out layer. Generally the higher crystalline hydroxyapatite will have a crystallinity of from about 60% to about 90%, more particularly from about 80% to about 85%. Typically the lower crystalline hydroxyapatite will have a crystallinity of less than about 50%.

It is believed that in this arrangement, the lower crystallinity hydroxyapatite in the second outer layer will resorb in the body quickly while the hydroxyapatite in the first outer layer will either not resorb or will only resorb slowly. In one arrangement, the crystallinity of the hydroxyapatite in the second outer layer may resorb in a matter of weeks, with from about 2 to about 8 weeks being indicative of the time period, and with from about 4 to about 6 weeks being preferred. In contrast, the resorbtion of the hydroxyapatite in the first outer layer being of higher crystallinity, if it resorbs at all, will do so in a time period of years rather than weeks. Generally a resorbtion period of from 8 to about 15 years can be expected with from about 10 to about 12 years being desirable. It will however be understood that in addition to the crystallinity, particle size and in vivo loading will impact on the resorbtion period.

The presence of the bone ingrowth material offers various advantages in addition to promoting bone ingrowth. Since the outer layers comprise pores, they can be structurally weak in compression which can reduce the strength of the prosthesis in compression which can result in difficulties at the time of insertion. The presence of the bone ingrowth material within the pores provides improved strength and enables the prosthesis to withstand the rigors of insertion. In this connection it is noteworthy that impaction forces where the prosthesis is an acetabular prosthesis can be of the order of 5 to 20 mPa. Further the bone ingrowth material will generally be stiffer than the surrounding polyaryletherketone and therefore will assist in providing the required rigidity for impaction. The resorbtion of at least some of the bone ingrowth material in the second outer layer within weeks of implantation means that that the stiffness of the prosthesis is reduced and becomes closer to that of the natural bone offering the advantages discussed above.

It will be understood that as the bone replaces the resorbed material to promote bone ingrowth it integrates into the porous structure.

The pores in the outer layers may be of any suitable size. In one arrangement the pore size will be in the region of about 300 to about 500 microns.

Any suitable amount of pores in the outer layers may be present. The amount of pores in the first and second outer layers may be the same or different. Generally a porosity of from about 50 to about 90% may be used. Although the strength of the outer layer(s) may be reduced at the higher porosity, the strength required to withstand impaction of the prosthesis in the bone may be provided by reinforcement and/or the presence of the material to promote osteointegration.

According to a second aspect of the present invention there is provided a prosthesis comprising:
  an inner layer formed from a polyaryletherketone;
  a first outer layer adjacent to said inner layer formed from a porous polyaryletherketone, at least some of said pores having located therein material to promote osteointegration having a crystallinity of from about 60% to about 90%; and
  a second outer layer adjacent to said first outer layer formed from a porous polyaryletherketone, at least a portion of said pores having located therein material to promote osteointegration having a crystallinity of less than about 50%.

In one arrangement substantially all of the pores in either or both layers may have material to promote osteointegration located therein of the specified crystallinity.

The prosthesis is preferably an acetabular prosthesis. In one arrangement it may be of a conventional cup shape. However, since in the natural pelvis the acetabulum is not a hemisphere and is more akin to a horseshoe shape, the prosthesis may be of a similar horseshoe shape. It is known that even when a cup shaped prosthesis is used, the wear on the cup by the femoral head prosthesis subscribes a horseshoe.

In one alternative arrangement the prosthesis may be of a combination structure whereby the cup is overall of conventional hemispherical cup but is thicker in the bearing region, i.e. in the horseshoe, and thinner in the remaining area. This thinner area may be the location of fixing means to the bone. Thus where bone screws are to be used, they may be inserted through the prosthesis at this position. Where a combination structure is used, the outer surface may generally be a conventional hemispherical cup and the increased thickness in the bearing region will lead to a raised bearing surface in the inner surface of the cup.

The prosthesis of the present invention when of a conventional hemispherical structure will be of any suitable size and the walls of any suitable thickness. The thickness will generally be the minimum required to conserve bone and maintain as much of the natural femur head diameter as possible. In one arrangement, the wall thickness will be from about 2 to about 5 mm with about 3 mm being generally useful. The ratio of the thickness of the inner layer to the outer layer may be adjusted as required. However, it is believe that a ratio in the region of 1:1 may be desirable. However a variation in the thickness ratio allows the properties of the prosthesis to be tailored such that the natural distribution of loads into the pelvis is replicated.

Where the prosthesis is of the arrangement where there is an increased thickness in the load bearing area and a thinner area in non-load bearing positions, the thickness of the load bearing area will be similar to that discussed above for conventional prostheses.

The prosthesis of the present invention may be formed by any suitable means. In one arrangement, the layered structure may be made by an injection moulding process. The pores in the outer layers are formed by mixing a sacrificial material in pellet form with pellets of the polyaryletherketone. Once the layer is formed, the sacrificial material is removed by appropriate means. In one example, the material to promote bone ingrowth, such as hydroxyapetite pellets, may be mixed with pellets of the polyaryletherketone. Once the layer has been injection moulded and cured, an etchant, such as an acid may be applied to the outermost surface of the second outer layer to preferentially burn off some of the material to promote osteointegration to form the pores in the second outer layer which will not include the material to promote osteointegration. Since the acid is applied to the outer surface of the prosthesis, the sacrificial material will be substantially removed from the second outer layer to provide the pores. However, the amount of acid used will be selected such that it little or no acid penetrates through to the first outer layer such that material to promote osteointegration is maintained in the pores.

Thus according to a third aspect of the present invention there is provided, a process for manufacturing the prosthesis of the above first aspect comprising the steps of:
  forming an inner layer of polyaryletherketone by injection moulding;
  mixing pellets of material to promote osteointegration with pellets of polyaryletherketone;
  forming the first and second outer layers on the inner layer by injection moulding; and
  applying an etchant material to the surface of the second outer layer such that the material to promote osteointegration is removed from at least some of the pores.

Any suitable etchant may be used. Suitable etchants include acids such as nitric acid or citric acid.

In one alternative arrangement, the porous outer layer may be made by selective laser beam melting, selective electron beam melting or selective sintering with selective laser beam melting being particularly preferred. Selective laser melting is a two-dimensional production process resulting in a three dimensional solid object. The direct laser melting process entails spreading a thin layer of a polyaryletherketone powder across an area on a substrate where an upstanding portion is to be built. A cross section of the layer is then selectively "drawn" on the layer of powder using energy from a laser. The laser fuses the powder so as to form a first layer of the eventual outer layer. This sequence of operations is then repeated as often as required until the desired shape has been created. An offset technique allows, for example bridges to be formed, leading to the desired porous structure.

Electron beam melting is a similar procedure except that an electron beam is used instead of a laser to effect fusion of the powder. The electron beam is focused using a series of electromagnets in a similar manner to that used to control the electron beam in a conventional television set.

Selective laser sintering is another process that can be used to build up the outer layer. A laser beam is used to "draw" the desired layer outline and results in fusion of the polymer in the area which has been illuminated by the laser beam. As with laser melting and electron beam melting processes the outer layer is built up from many layers. Subsequent sintering and hipping of the layers result in pyrolysis of the polymer to form the desired outer layer.

In the processes for forming the first and second outer layers do not include using the material to promote osteointegration as sacrificial means of forming the pores, the material can be applied by any suitable means including by plasma spraying.

The present invention will now be described, by way of example, with reference to the accompanying drawings in which.

Figure 1:
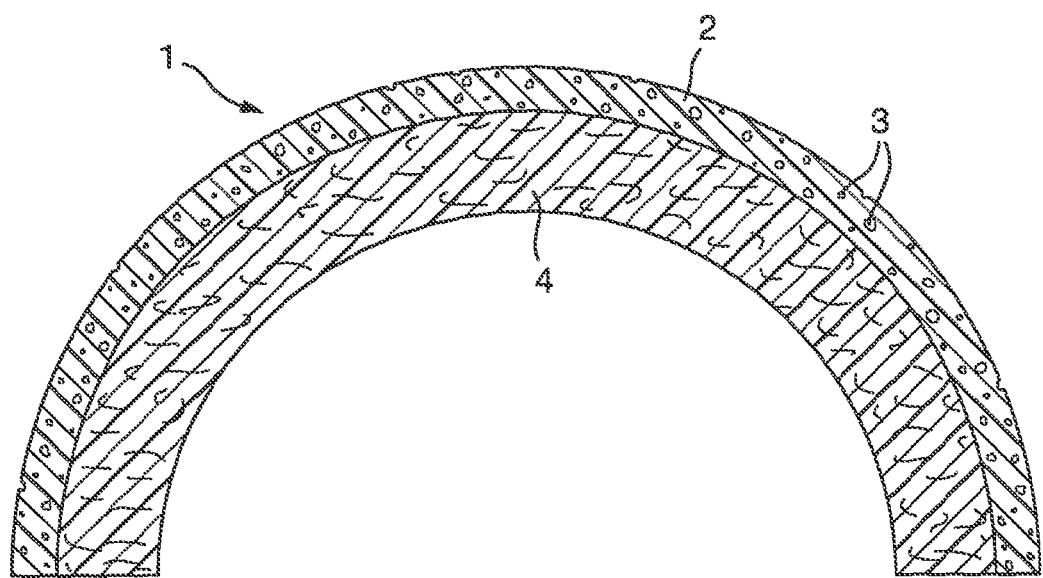
FIG. 1 is a cross section through an acetabular prosthesis according to a first aspect of the present invention.

As illustrated in FIG. 1, the acetabular prosthesis 1 of the present invention comprises an outer layer 2 comprising porous polyetheretherketone. Although not illustrated this outer layer comprises a first outer layer and a second outer layer. In this example the first and second outer layers are contiguous. The layer comprises a plurality of pores 3, at least some of which are interconnected. The cup 1 also includes an inner layer 4 comprising carbon fibre reinforced polyetheretherketone. Hydroxyapatite is located in at least some of the pores in the first outer layer and at least some of the pores in the second outer layer are free of hydroxyapatite.

Figure 2:
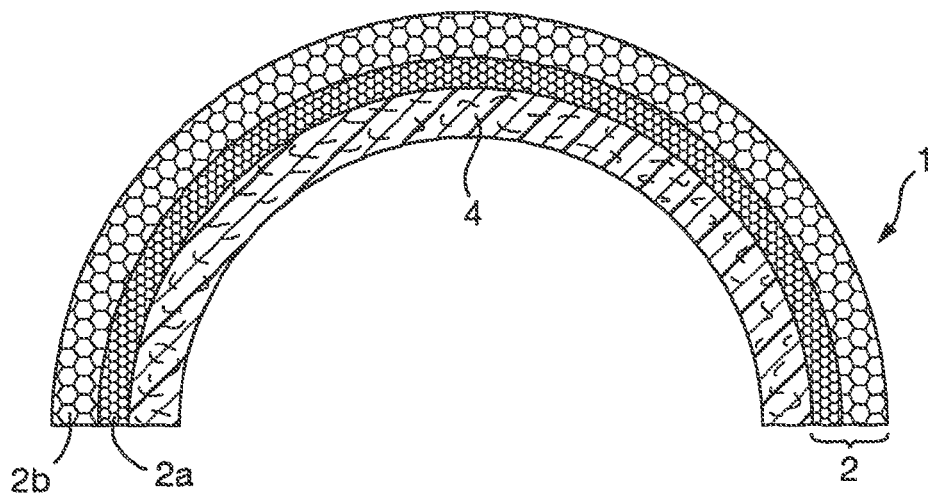
FIG. 2 is a cross section through an acetabular prosthesis according to a second aspect of the present invention.
Figure 2A:
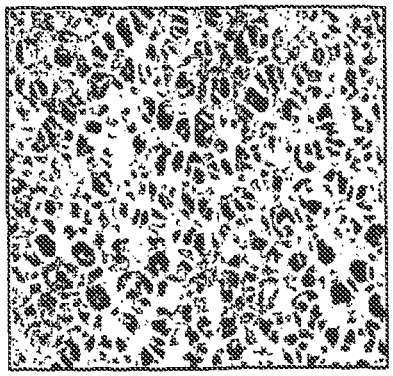
FIG. 2a is a close up of the material forming the first outer layer.
Figure 2B:
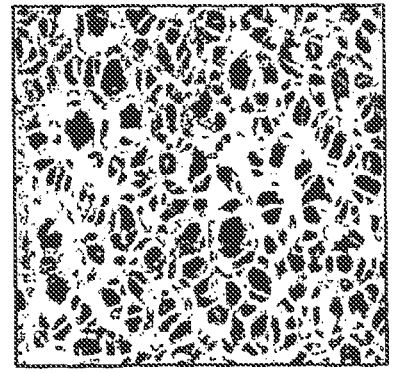
FIG. 2b is a close up of the material forming the second outer layer.

An alternative arrangement is illustrated in FIG. 2. In this arrangement the cup 1 comprises an inner layer 4 of carbon fibre reinforced polyetheretherketone. The outer layer 2 is comprised of a first outer layer 2a and a second outer layer 2b. Although in FIG. 2 there is honeycombed shading this is simply to differentiate the layers in the figure and is not indicative of any structure. Examples of the pores in the layers are illustrated in FIGS. 2a and 2b respectively. In this embodiment the hydroxyapatite present as the material to promote osteointegration has been applied by plasma coating and as such the walls of the pores which are on the line of sight from the application of the coating are coated. In this embodiment the crystallinity of the hydroxyapatite in the first outer layer is of a higher crystallinity than that in the second outer layer.

Figure 3:
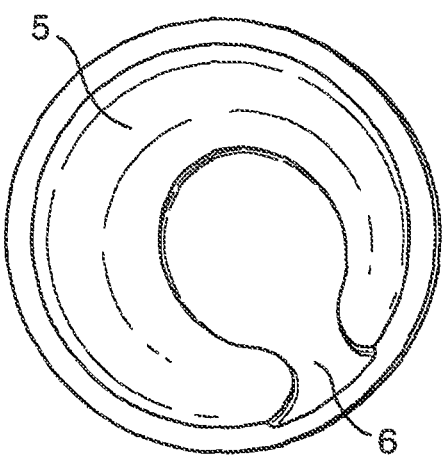
FIG. 3 is a perspective view of an acetabular prosthesis of the present invention illustrating an embodiment having a raised bearing surface.

The cup 1 may be a conventional hemispherical cup prosthesis or as illustrated in FIG. 3, the prosthesis may have a raised bearing surface 5 on the inner surface. A thinner area is located in region 6. Fixation screws may be passed through this thinner area.

Figure 4:
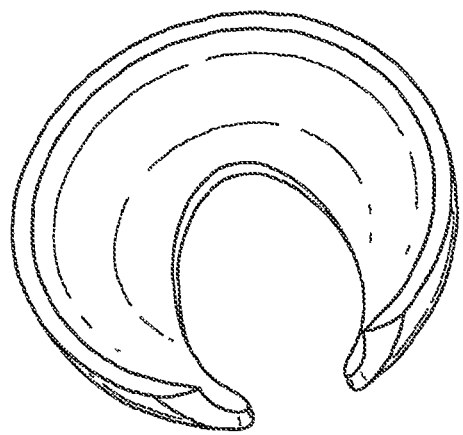
FIG. 4 is a perspective view of anacetabular prosthesis of the present invention illustrating an embodiment of a horseshoe configuration.

In an alternative arrangement the prosthesis may be of the horseshoe configuration as illustrated in FIG. 4.

Whilst the present invention has been discussed in detail in connection with an acetabular prosthesis, it will be understood that the invention may be applied to other prosthesis such as prosthesis in the shoulder. Further, it will be understood that various modifications, uses or adaptations of the invention may be made within the scope of this invention.

The invention claimed is:

1. A process for manufacturing a prosthesis, comprising the steps of:
    forming an inner layer of polyaryletherketone by injection molding;
    mixing pellets of bone ingrowth material with pellets of polyaryletherketone to form a material;
    forming a first outer layer of the material on the inner layer by injection molding;
    forming a second outer layer of the material on the first outer layer by injection molding; and
    applying an etchant material to the surface of the second outer layer such that the bone ingrowth material is removed from at least some pores in the second outer layer and wherein the etchant is an acid and the amount used is selected so no acid penetrates through to the first outer layer.

2. The process of claim 1, wherein the crystallinity of the material to promote osteointegration in the first outer layer is from about 60% to about 90%.

3. The process of claim 1, wherein the crystallinity of the material to promote osteointegration in the first outer layer is from about 80% to about 85%.

4. The process of claim 1, wherein the crystallinity of the material to promote osteointegration in the second outer layer is less than 50%.

5. The process of claim 1, wherein the prosthesis is an acetabular cup.

6. The process of claim 1, wherein the polyaryletherketone in the outer layers and the inner layer are the same.

7. The process of claim 1, wherein the polyaryletherketone in the outer layers and the inner layer are different.

8. The process of claim 1, wherein the pellets of bone ingrowth material are hydroxyapatite pellets.

* * * * *